(12) United States Patent
Sha (10) Patent No.: US 11,700,856 B2
(45) Date of Patent: Jul. 18, 2023

(54) MICROBIAL AGENT YF FAVORABLE FOR GROWTH OF CORN IN SALINE-ALKALI LAND, AND USE THEREOF

(71) Applicant: INSTITUTE OF PLANT PROTECTION, NINGXIA ACADEMY OF AGRICULTURE AND FORESTRY SCIENCES (KEY LABORATORY OF NINGXIA PLANT DISEASE AND INSECT PESTS CONTROL), Yinchuan (CN)

(72) Inventor: Yuexia Sha, Yinchuan (CN)

(73) Assignee: INSTITUTE OF PLANT PROTECTION, NINGXIA ACADEMY OF AGRICULTURE AND FORESTRY SCIENCES (KEY LABORATORY OF NINGXIA PLANT DISEASE AND INSECT PESTS CONTROL), Yinchuan (CN)

( * ) Notice: Subject to any disclaimer, the term of this patent is extended or adjusted under 35 U.S.C. 154(b) by 0 days.

(21) Appl. No.: 17/624,209

(22) PCT Filed: Feb. 20, 2021

(86) PCT No.: PCT/CN2021/077128
§ 371 (c)(1),
(2) Date: Dec. 30, 2021

(87) PCT Pub. No.: WO2021/185021
PCT Pub. Date: Sep. 23, 2021

(65) Prior Publication Data
US 2023/0075076 A1    Mar. 9, 2023

(30) Foreign Application Priority Data
Mar. 19, 2020   (CN) .......................... 202010198243.6

(51) Int. Cl.
*A01N 63/20* (2020.01)
*A01P 1/00* (2006.01)
*A01P 3/00* (2006.01)
*A01P 21/00* (2006.01)
*C12N 1/20* (2006.01)
*A01N 63/22* (2020.01)

(52) U.S. Cl.
CPC ............. *A01N 63/20* (2020.01); *C12N 1/205* (2021.05)

(58) Field of Classification Search
None
See application file for complete search history.

(56) References Cited

FOREIGN PATENT DOCUMENTS

| CN | 106947725 A | 7/2017 |
|---|---|---|
| CN | 109082398 A | 12/2018 |
| CN | 110373207 A | 10/2019 |
| CN | 111304132 A | 6/2020 |
| KR | 102039229 B1 | 10/2019 |
| WO | 2015118516 A1 | 8/2015 |

OTHER PUBLICATIONS

The China National Intelleectual Property Administration (CNIPA) The First Office Action for 202010198243.6 Feb. 22, 2021 10 Pages (including translation).
World Intelllectual Property Organization (WIPO) International Search Report for PCT/CN2021/077128 May 24, 2021 8 Pages (including translation).
Wu Xiaowei et al. "Breeding and compounding of salt-and alkali-tolerant microbial complex microbial inoculum and its improvement effect on saline-alkali soil", Jiangsu Agricultural Sciences, vol. 43, No. 6. Jun. 25, 2015 pp. 346-349.
Wang CQ et al. "Effects of Bacillus velezensis FKMIO for Promoting the Growth of Malus hupehensis Rehd. and Inhibiting Fusarium verticillioides" Front Microbio, vol. 10, No. 1, Jan. 10, 2020 Document No. 2889.
Sha YX et al. "Impact of seed soaked by Bacillus on endophytic bacterial community structure of rice" ACTA Ecologica Sinica, vol. 39, No. 22, Nov. 2019.
Sha YX et al. "Microbial Agents Mixed with Saline-alkaline Soil: Effect of Prevention of Stem Basal Rot and Growth-promoting on Maize" Chinese Agricultural Science Bulletin, vol. 37, No. 5, Feb. 15, 2021 pp. 75-82.

*Primary Examiner* — Alton N Pryor
(74) *Attorney, Agent, or Firm* — Anova Law Group, PLLC (57) ABSTRACT

The present disclosure provides a microbial agent YF, including four strains: *Bacillus sonorensis* B-2, *Bacillus paralicheniformis* B-26, *Bacillus sonorensis* N-16, and *Bacillus pumilus* N-17. The four strains were all deposited in the China General Microbiological Culture Collection Center (CGMCC) on Mar. 5, 2020. The *Bacillus sonorensis* B-2 has a deposit accession number of CGMCC NO. 19454, the *Bacillus paralicheniformis* B-26 has a deposit accession number of CGMCC NO. 19449, the *Bacillus sonorensis* N-16 has a deposit accession number of CGMCC NO. 19448, and the *Bacillus pumilus* N-17 has a deposit accession number of CGMCC NO. 19450. The microbial agent provided by the present disclosure can effectively prevent stem rot of corn in saline-alkali land, improve the quality of saline-alkali land, and significantly promote the growth of corn.

14 Claims, 9 Drawing Sheets
Specification includes a Sequence Listing.

```
                       SEQUENCE LISTING

<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: Bacterial amplification primer 338F

<400> SEQUENCE: 1
actcctacgg gaggcagca                                                19

<210> SEQ ID NO 2
<211> LENGTH: 20
<212> TYPE: DNA
<213> ORGANISM: Artificial Sequence
<220> FEATURE:
<223> OTHER INFORMATION: Bacterial amplification primer 806R

<400> SEQUENCE: 2
ggactachvg ggtwtctaat                                               20

<210> SEQ ID NO 3
<211> LENGTH: 19
<212> TYPE: DNA
<213> ORGANISM: Artificial Sequence
```

```
<220> FEATURE:
<223> OTHER INFORMATION: Fungal amplification primer ITS1F

<400> SEQUENCE: 3
tccgtaggtg aacctgcgc                                                19

<210> SEQ ID NO 4
<211> LENGTH: 20
<212> TYPE: DNA
<213> ORGANISM: Artificial Sequence
<220> FEATURE:
<223> OTHER INFORMATION: Fungal amplification primer ITS2R

<400> SEQUENCE: 4
ctcggacgag gatcctcgcc                                               20
```

MICROBIAL AGENT YF FAVORABLE FOR GROWTH OF CORN IN SALINE-ALKALI LAND, AND USE THEREOF

CROSS-REFERENCE TO RELATED APPLICATIONS

The present disclosure is a National Stage Application under 35 U.S.C. § 371 of PCT International Application No. PCT/CN2021/077128 filed Feb. 20, 2021, which claims priority to Chinese Patent Application No. 202010198243.6 filed to the China National Intellectual Property Administration (CNIPA) on Mar. 19, 2020 and entitled "MICROBIAL AGENT YF FAVORABLE FOR GROWTH OF CORN IN SALINE-ALKALI LAND, AND USE THEREOF", all of which are incorporated herein by reference in entirety.

REFERENCE TO AN ELECTRONIC SEQUENCE LISTING

The contents of the electronic sequence listing (24243sequencelisting_ST25.txt; Size: 2 kilobytes; and Date of Creation: Oct. 27, 2022) is herein incorporated by reference in its entirety.

TECHNICAL FIELD

The present disclosure relates to the technical field of microorganisms, and in particular to use of a microbial agent YF in promoting the growth of corn in saline-alkali land and the prevention and treatment of stem rot.

BACKGROUND

Saline-alkali land is an important land resource. The improvement and utilization of saline-alkali land has always been a focus and a hot spot in the field of agricultural research, and is also a basis for the development of reserve resources of arable land and the potential guarantee of increased grain production in China. Globally, an area of saline-alkali land accounts for 10% of a total area of land. A total area of saline-alkali land that has an impact on arable land in China exceeds 500 million mu, and China has an area of saline-alkali land ranking the third among all countries worldwide. In China, an area of saline-alkali land with agricultural development potential accounts for greater than 10% of a total area of arable land. Saline-alkali land generally has a high pH, and an excessively-high salt concentration can cause soil degradation, change soil permeability and matrix potential, and reduce soil microbial activity, thereby posing a great threat to grain production. At present, the physical, chemical, and biological methods are mainly used to repair saline-alkali land. These methods require high cost and can hardy fundamentally solve the problem of soil salinization. In order to solve this problem, the soil quality needs to be considered. It is believed by scholars that microbial fertilizers can fundamentally improve the soil quality. As more and more attention is paid to the ecological environment and land resources are increasingly scarce, the present disclosure of microbial agents with natural soil microorganisms as the main component has attracted wider attention in the saline-alkali agriculture. Microbial agents can not only improve the quality of soil, but also repair saline-alkali land in combination with plants. Moreover, microbial agents, when applied to corn, tomato, chickpea, and other plants, can well prevent diseases and insects and promote growth, increase a protein content, a soluble sugar content, and the like, and enhance the absorption of minerals and nitrogen.

Corn is an important grain crop worldwide, and has a planting scale second only to wheat. With changes in global climate conditions, continuous cropping, high-density cultivation, etc., the ecological environment of corn fields has changed, the community structure of dominant bacteria among pathogens in the soil has changed, the accumulation of diseased plants is increasing, and the community structure and the number of beneficial microorganisms have also changed greatly. These factors lead to imbalance of the soil microbial community structure in corn fields and more and more frequent occurrence of corn stem rot.

Corn stem rot is a typical soil-borne disease caused by the mixed infection multiple pathogens, and is one of the main diseases that endanger the corn production worldwide. Generally, corn stem rot can cause a production loss of 10% to 25% and even of 75% in severe cases. Resistant varieties, chemical seed coating agents, and increased application of potassium fertilizer are the main measures used in current production. However, the select breeding of resistant varieties takes a long time, and residual chemical seed coating agents can easily pollute the ecological environment, threaten human health, aggravate soil salination, and make pathogens have resistance. Reducing the number of pathogens in soil and interfering with the soil microecological environment where the pathogens grow are the key means to prevent and treat corn stem rot. Therefore, the research of microbial agents for corn stem rot has important scientific significance and application value for food safety and sustainable development of the corn industry.

It is well known that there are many pathogens in soil, the quantity and activity of the pathogens affect the stability of the soil microbial community structure, and the imbalance of the soil microbial ecological environment will aggravate the hazard of crop soil-borne diseases. Studies have shown that agronomic measures and biological agents have a significant impact on the diversity and population composition of the soil microbial community. Microbial agents are widely used to improve the ecological environment of soil microorganisms to achieve the effects of disease prevention, insect prevention, growth promotion, and yield increase. Lv Ning, et al. found that a *Bacillus subtilis* (*B. subtilis*) wettable powder showed a significant prevention and treatment effect on Cotton Verticillium Wilt when applied dropwise, and the number and species abundance of soil fungi, bacteria, and actinomycetes significantly increased with the increase in the application amount of the wettable powder. Chen, et al. mixed a *Trichoderma asperellum* (*T asperellum*) granule with a chemical fertilizer and applied a resulting mixture into the soil before sowing, which showed a significant control effect on corn stem rot. However, there are few microbial agents that can be used for the growth promotion and disease control of corn in saline-alkali land. It is necessary to develop a microbial agent beneficial for the growth of corn and the prevention and treatment of corn stem rot in saline-alkali land.

SUMMARY

In order to solve the above-mentioned technical problems in agricultural production and the deficiencies of the prior art, the present disclosure provides a compound microbial agent that is beneficial to the growth or corn in saline-alkali land and shows a prominent prevention and treatment effect on corn stem rot in saline-alkali land.

In order to achieve the above objective, the present disclosure adopts the following technical solutions:

In a first aspect, the present disclosure provides a microbial agent YF, including the following four strains: *Bacillus sonorensis* B-2. *Bacillus paralicheniformis* B-26. *Bacillus sonorensis* N-16, and *Bacillus pumilus* N-17. The four strains were all deposited in the China General Microbiological Culture Collection Center (CGMCC), at No. 3. Courtyard 1, Beichen West Road, Chaoyang District, Beijing, with deposit date of Mar. 5, 2020. The *Bacillus sonorensis* B-2 has a deposit accession number of CGMCC. NO. 19454, the *Bacillus paralicheniformis* B-26 has a deposit accession number of CGMCC NO. 19449, the *Bacillus sonorensis* N-16 has a deposit accession number of CGMCC NO. 19448, and the *Bacillus pumilus* N-17 has a deposit accession number of CGMCC NO. 19450. Growth conditions suitable for the four strains include: temperature: 30° C. to 37° C., pH greater than 8.0, and Horikoshi I, improved LB-I or improved LB-II medium.

The *Bacillus sonorensis* B-2, the *Bacillus paralicheniformis* B-26, the *Bacillus sonorensis* N-16, and the *Bacillus pumilus* N-17 may be at a mass ratio of 1:1:1:1; and a viable count of *Bacillus* in the microbial agent YF may be greater than 1 billion CFU/g.

In a second aspect, the present disclosure provides a microbial agent YF; the microbial agent includes a bacterial powder prepared from the four strains described above and the microbial agent YF further includes a carrier, humic acid, a conditioning agent, and trace elements; and the content of each component in the Microbial agent YF may include: 48% to 58% of the bacterial powder, 35% to 45% of the carrier, 3% to 8% of the humic acid, 0.4% to 1.2% of the conditioning agent, and 0.6% to 1.8% of the trace elements.

The carrier may be sheep dung; the conditioning agent may be calcium sulfate ($CaSO_4 \cdot 2H_2O$; and the trace elements may include zinc sulfate ($ZnSO_4$), ferrous sulfate ($FeSO_4 \cdot 7H_2O$), and potassium sulfate ($K_2SO_4$).

The content of each component in the microbial agent YF may include: 48% to 58% of the bacterial powder, 35% to 45% of the carrier, 3% to 8% of the humic acid, 0.4% to 1.2% of the calcium sulfate, 0.2% to 0.6% of the zinc sulfate, 0.2% to 0.6% of the ferrous sulfate, and 0.2% to 0.6% of the potassium sulfate.

The carrier may be decomposed sheep dung.

The content of each component in the microbial agent YF may include: 54% of the bacterial powder, 40% of the carrier, 5% of the humic acid, 0.4% of the calcium sulfate, 0.2% of the zinc sulfate, 0.2% of the ferrous sulfate, and 0.2% of the potassium sulfate.

In a third aspect, the present disclosure provides use of the microbial agent YF in the preparation of a drug for preventing and treating stem rot of corn in saline-alkali land.

In order to achieve the above objectives, the present disclosure provides a microbial agent YF, including *B. sonorensis* B-2, *B. paralicheniformis* B-26. *B. sonorensis* N-16, and *B. pumilus* N-17. The *B. sonorensis* B-2, the *B. paralicheniformis* B-26, the *B. sonorensis* N-16, and the *B. pumilus* N-17 may be at a mass ratio of 1:1:1:1, and a viable count of *Bacillus* in the microbial agent YF may be greater than 1 billion. CFU/g. The microbial agent YF has prominent effect.

In the microbial agent YF, the functional bacteria are isolated from the saline-alkali soil, which has high saline tolerance and can lower a soil pH, improve a soil nutritional status, and has well prevent disease and promote growth effects; humic acid can increase fertilizer efficiency, improve soil, and promote plant growth, and often used as an adjuvant for a microbial fertilizer; the carrier is sheep dung, which is widely available and cost-effective; the calcium sulfate is a soil improvement agent for saline-alkali land (Wang Minghua. Effect of Improvement Agent on Soda Saline-Alkali Land and Physiological Characteristics of Corn. Harbin: Northeast Agricultural University, 2016.); and all trace elements are nutrient elements to enhance the resistance of corn plants to corn stem rot (Li Baojun, Zhang Lansong, Zhu Jing, et al. Effect of Nitrogen, Phosphorus, Potassium, and Zinc on Corn Stem Rot and Yield. Hebei Agricultural Sciences, 2016, 20 (4): 41-44; Wang Xiaoming, Wu Quanan, Zhang Peikun. Research on Prevention and Treatment of Corn Stem Rot by Zinc Sulfate. Plant Protection, 1999. (2): 23-25.)

The present disclosure has the following beneficial effects.

The microbial agent YF provided by the present disclosure has a prominent control effect on corn stem rot in saline-alkali land, and can significantly inhibit a variety of soil-borne plant pathogens; the microbial agent also shows an obvious microecological regulation effect on the soil of corn fields in saline-alkali land, improving, the diversity and structure of fungal and bacterial communities in soil and reducing the abundance of pathogens in soil; the microbial agent can also well improve the soil of corn fields in saline-alkali land, effectively reducing a soil pH and increasing the contents of organic carbon, nitrate nitrogen, total nitrogen, and available potassium: the microbial agent can also significantly promote the growth of corn, increasing a corn emergence rate by 107.75%, a corn plant height by 46.68%, and a corn stem thickness by 48.54%; and the microbial agent can significantly increase the number of productive ears, an ear thickness, an ear length, and an ear weight and reduce a bald rate for corn. The microbial agent YF of the present disclosure does not include pathogens, heavy metals, and toxic chemical substances, and thus can be used to treat the soil for corn cultivation without causing additional burden on the soil, which is environmentally-friendly. The microbial agent has important scientific significance and application value for the sustainable development of corn industry and the effective utilization of saline-alkali land resources.

BRIEF DESCRIPTION OF THE DRAWINGS

The accompanying drawings which constitute a part of the present disclosure provide further comprehension of the present disclosure. The schematic examples of the present disclosure and description thereof are intended to explain the present disclosure and do not constitute an improper limitation to the present disclosure. In the accompanying drawings.

DETAILED DESCRIPTION

In order to make the objectives, technical solutions, and advantages of the examples of the present disclosure clearer, the technical solutions in the examples of the present disclosure are described clearly and completely below. Apparently, the described examples are some rather than all of the examples of the present disclosure. All other examples obtained by a person of ordinary skill in the art based on the examples of the present disclosure without creative efforts shall fall within the protection scope of the present disclosure. It should be noted that the examples in the present disclosure or features in the examples may be combined arbitrarily in a non-conflicting manner.

The present disclosure provides a microbial agent YF, including the following four strains: *B. sonorensis* B-2, *B. paralicheniformis* B-26, *B. sonorensis* N-16, and *B. pumilus* N-17. The four strains were all deposited in the China General Microbiological Culture Collection Center (CGMCC) on Mar. 5, 2020. The *B. sonorensis* B-2 has a deposit accession number of CGMCC NO. 19454, the *B. paralicheniformis* B-26 has a deposit accession number of CGMCC NO. 19449, the *B. sonorensis* N-16 has a deposit accession number of CGMCC NO. 19448, and the *B. pumilus* N-17 has a deposit accession number of CGMCC NO. 19450. Growth conditions suitable for the four strains include: temperature: 30° C. to 37° C., pH greater than 8.0, and Horikoshi I, improved LB-I or improved LB-II medium.

The *B. sonorensis* B-2, the *B. paralicheniformis* B-26, the *B. sonorensis* N-16, and the *B. pumilus* N-17 may be at a mass ratio of 1:1:1:1; and a viable count of *Bacillus* in the microbial agent YF may be greater than 1 billion CFU/g.

The present disclosure provides a microbial agent YF, which includes a bacterial powder prepared from the four strains described above and further includes a carrier, humic acid, a conditioning agent, and trace elements; and the content of each component in the microbial agent YF may include: 48% to 58% of the bacterial powder, 35% to 45% of the carrier, 3% to 8% of the humic acid, 0.4% to 1.2% of the conditioning agent, and 0.6% to 1.8% of the trace elements.

The carrier may be sheep dung and preferably decomposed sheep dung.

The conditioning agent may be calcium sulfate ($CaSO_4 \cdot 2H_2O$); and the trace elements may include zinc sulfate ($ZnSO_4$), ferrous sulfide ($FeSO_4 \cdot 7H_2O$), and potassium sulfate ($K_2SO_4$).

The content of each component in the microbial agent YF may include: 48% to 58% of the bacterial powder, 35% to 45% of the carrier, 3% to 8% of the humic acid, 0.4% to 1.2% of the calcium sulfate, 0.2% to 0.6% of the zinc sulfate, 0.2% to 0.6% of the ferrous sulfate, and 0.2% to 0.6% of the potassium sulfate. Preferably, the content of each component in the microbial agent YF may include: 54% of the bacterial powder, 40% of the carrier, 5% of the humic acid, 0.4% of the calcium sulfate, 0.2% of the zinc sulfate, 0.2% of the ferrous sulfate, and 0.2% of the potassium sulfate.

Example 1 Preparation of Four Strains (1) Isolation of *Bacillus Halophilus* and *Bacillus Alcalophilus*

Isolation of *Bacillus halophilus*: Soil in a corn field in saline-alkali land of Pingluo County, Ningxia Hui Autonomous Region was collected, 10 g of the sample was added to 100 mL of sterile water, and a resulting mixture was thoroughly shaken for about 15 min to allow uniform dispersion of soil particles. The sample was then serially diluted with sterile water. Diluted sample solutions with concentrations of $10^{-2}$, $10^{-3}$, $10^{-4}$, $10^{-5}$, and $10^{-6}$ (each 0.1 mL) were coated on Horikoshi I, improved LB-I or improved LB-II media with different NaCl concentrations, and coated plates were wrapped with a sealing film and placed upside down in a 37° C. incubator for cultivation. After 3 d to 7 d of cultivation, single colonies with different phenotypic characteristics were picked and streaked for gradient separation to obtain pure strains. Single colonies of a purified strain were picked, transferred to 40% glycerol, and stored in an ultra-low temperature refrigerator at −80° C. for later use.

Isolation of *Bacillus alcalophilus*: Soil in a corn field in saline-alkali land of Guyuan City, Ningxia Hui Autonomous Region was collected and the soil samples were subjected to a water bath at 80° C. for 10 min, and then the dilution plate coating method was used to achieve isolation on Horikoshi I, improved LB-I or improved LB-II media. The morphology was observed for colonies on each plate, and different colonies were distinguished and numbered according to size, color, dryness and wetness, shape, edge, transparency, and other characteristics of colonies. Single colonies with different colony morphologies were picked for continuous streak cultivation to obtain pure strains, and the strains were cryopreserved with glycerol at −80° C.

Horikoshi I medium (g/L): glucose: 10.0 g, peptone: 5.0 g, yeast extract: 5.0 g, $K_2HPO_4$: 1.0 g, $MgSO_4$: 0.2 g, $Na_2CO_3$: 10.0 g (sterilized separately), and agar: 15.0 g to 20.0 g, pH 9, sterilized at 121° C. for 20 min.

Improved LB-I medium (75.0 g/L NaCl): tryptone: 10.0 g, yeast extract: 5.0 g, NaCl: 75.0 g, agar: 15 g to 20 g, and water: 1,000 mL, pH 9.0.

Improved LB-II medium (150.0 g/L NaCl): tryptone: 10.0 g, yeast extract: 5.0 g. NaCl: 150.0 g, agar: 15 g to 20 g, and water: 1,000 mL, pH 9.0. The above media all were sterilized in an autoclave at 121° C. for 20 min.

(2) Screening of Halophilic and Alkalophilic Antagonistic Bacteria

A. Screening of Halophilic and Alkalophilic Antagonistic Bacteria

*Fusarium oxysporum* (*F. oxysporum*), *Fusarium moniliforme* (*F. moniliforme*), *Fusarium oxysporum* f.sp. *niveum* (*F. oxysporum f.* sp. *niveum*), *Rhizoctonia solani* (*R. solani*), and *Phytophthora parasitica* var. *nicotianae* (*P. parasitica* var. *nicotianae*) blocks each were inoculated on the center of a PDA medium plate, and after pathogen colonies grew for 2 d, a test strain block (5 mm) was inoculated at both sides with a distance of 2 cm from a colony edge. *R. solani* was subjected to face-to-face cultivation with a tested strain. The cultivation was conducted in an incubator at 28° C. in the dark, and 4 replicates were set for each treatment. 2 d later, the diameter and inhibition zone were measured for pathogen colonies, and results were shown in Table 1.

TABLE 1

Antagonistic effects of halophilic and alkalophilic bacteria on a variety of soil-borne pathogens

| | Mycelium inhibition rate | | | |
|---|---|---|---|---|
| Pathogen | Antagonistic bacteria B-2 (%) | Antagonistic bacteria N-16 (%) | Antagonistic bacteria N-17 (%) | Antagonistic bacteria B-26 (%) |
| F. oxysporum | 44.00 | 36.84 | 40.91 | 41.50 |
| F. oxysporum f. sp. niveum | 70.27 | 76.32 | 70.00 | 54.02 |
| F. moniliforme | 64.89 | 37.50 | 38.89 | 60.61 |
| R. solani | 20.00 | 31.25 | 37.50 | 33.33 |
| P. parasitica var. nicotianae | 79.48 | 77.84 | 70.22 | 77.25 |
| Magnaporthe grisea (M. grisea) | 84.12 | 65.04 | 66.83 | 88.01 |

B. Enzyme-Producing Ability Tests for the Halophilic and Alkalophilic Antagonistic Bacteria Detection of amylase: Newly-activated single colonies were picked and inoculated on an LB plate with 0.2% soluble starch, and cultivated for 48 h until obvious colonies were formed; and Lugol's iodine was added dropwise on the plate to stain for 10 min, and then the plate was washed with 70% ethanol. For strains capable of producing amylase, a transparent circle formed around an area where colonies grow can be observed on a black background. If there is a transparent circle, it indicates that the strain can produce amylase. 3 replicates were set for each treatment. Results were shown in Table 2.

Detection of protease: An activated strain to be tested was puncturely inoculated on a 1% skimmed milk agar plate, and cultivated at 30° C.; and at 24 h, 48 h, and 72 h of cultivation, it was observed whether there is an outer transparent circle. If there is a transparent circle, it indicates that protease is produced. 3 replicates were set for each treatment. Results were shown in Table 2.

Detection of glucanase: A strain to be tested was inoculated on a plate with ABP medium, and cultivated at 30° C.; and at 48 h and 72 h of cultivation, it was observed whether there is a digestion circle on the plate. If there is a digestion circle, it indicates that glucanase is produced. 3 replicates were set for each treatment. Results were shown in Table 2.

Detection of siderophore by CAS medium: An activated strain to he tested was inoculated on a test CAS medium plate, and cultivated at 30° C. for 72 h; and then it was observed whether there is an orange halo on the plate. If there is an orange halo, it indicates that siderophore is produced. 3 replicates were set for each treatment. Results were shown in Table 2.

Detection of cellulase: An isolated strain was activated and then inoculated on a cellulose screening medium plate, and invertedly cultivated at 28° C. for 2 d; and then a 0.1% congo red staining solution was added to stain for 10 min, and then destaining was conducted for 5 min with 1 mol/L NaCl solution. If the strain produces cellulase, a clear transparent circle will appear around colonies. 3 replicates were set for each treatment. Results were shown in Table 2.

TABLE 2

Enzyme-producing ability of the halophilic and alkalophilic antagonistic bacteria Unit: cm

| Strain name | Amylase | Protease | Glucanase | Cellulase | Siderophore |
|---|---|---|---|---|---|
| Antagonistic strain B-2 | 2.10 | 0.52 | 0.54 | 0.67 | – |
| Antagonistic strain N-16 | 1.93 | 0.82 | — | 0.55 | – |
| Antagonistic strain N-17 | — | 0.7 | — | 0.73 | – |
| Antagonistic strain B-26 | 1.7 | 0.4 | 0.4 | 0.7 | + |

The number indicates a radius of a transparent circle, that is the enzyme-producing ability; and "-" indicates that such an enzyme is not produced.

(3) Identification of Halophilic and Alkalophilic Antagonistic Bacteria

Figure 1:
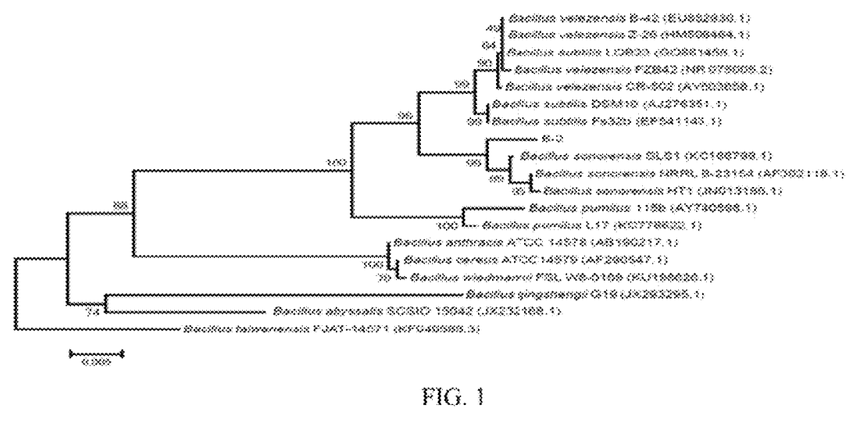
FIG. 1 is a phylogenetic tree of the strain B-2 based on 16S rDNA sequencing.
Figure 2:
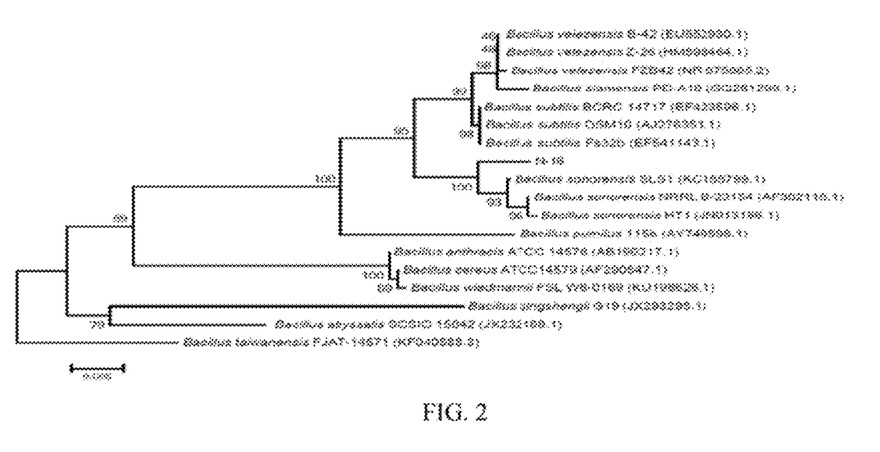
FIG. 2 is a phylogenetic tree of the strain N-16 based on 16S rDNA sequencing.
Figure 3:
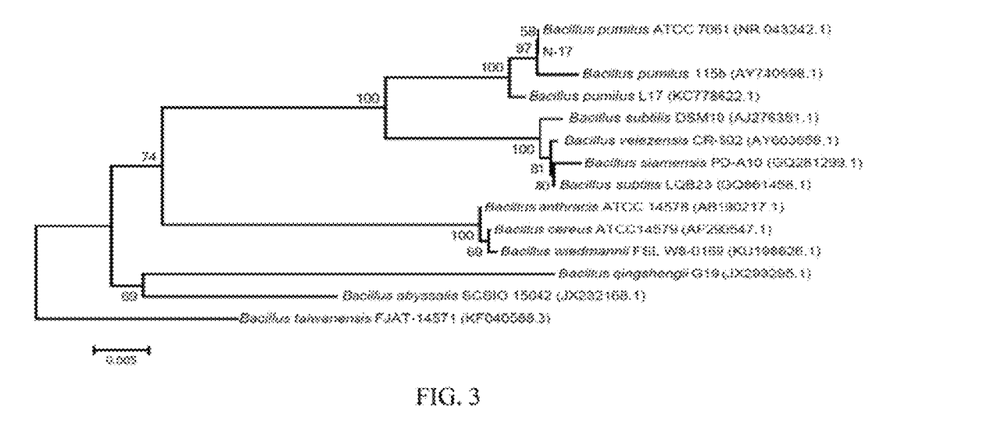
FIG. 3 is a phylogenetic tree of the strain N-17 based on 16S rDNA sequencing.
Figure 4:
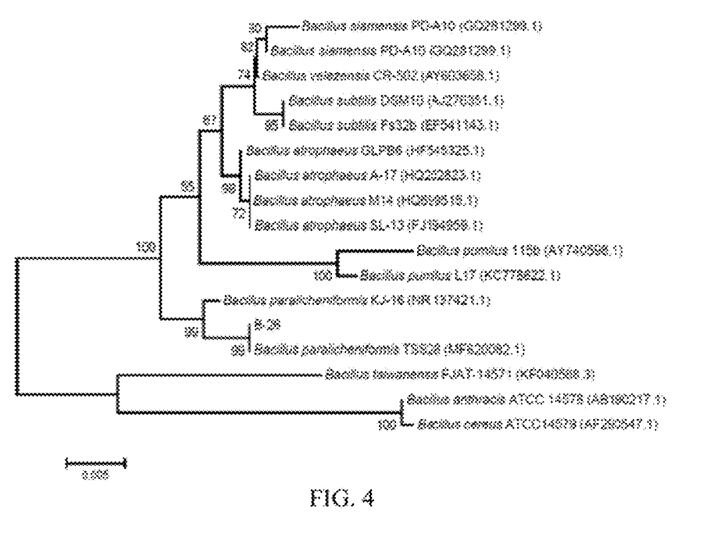
FIG. 4 is a phylogenetic tree of the strain B-26 based on 16S rDNA sequencing.
Figure 5:
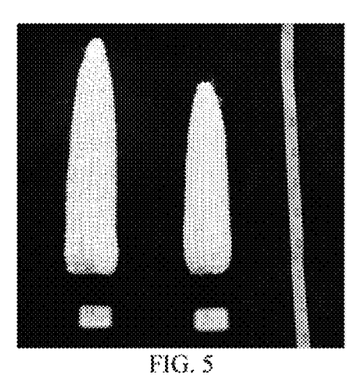
FIG. 5 is a picture of corn ears harvested.

In combination with the molecular biotechnology of 16S rDNA sequencing, morphological identification was conducted based on the "*Manual for Identification of Common Bacterial Systems*" to identify screened antagonistic bacteria. The strain B-2 was identified as *B. sonorensis*, as shown in FIG. 1; the strain N-16 was identified as *B. sonorensis*, as shown in FIG. 2; the strain N-17 was identified as *B. pumilus*, as shown in FIG. 3; and the strain B-26 was identified, as *B. paralicheniformis*, as shown in FIG. 4.

Example 2 Preparation of a Microbial Agent YF

1. Compatibility among halophilic and alkalophilic antagonistic bacteria: With reference to the Barbosa's determination method, half of an LB solid medium plate was streaked with one functional strain, and the other half was vertically streaked with another functional strain. 3 replicates were set for each treatment. The plates were incubated in a biochemical incubator at 37° C., and 24 h later, the compatibility between two strains was observed and recorded. Two strains without inhibition zones therebetween were considered compatible, and two strains with inhibition zones therebetween were considered incompatible. Compatibility results showed that the four strains did not inhibit each other.

LB liquid medium: yeast extract: 5 g, peptone: 10 g, sodium chloride: 5 g, and water: 1,000 ml, pH 7.4 to 7.6, sterilized at 121° C. for 30 min. LB solid medium: 15 g of an agar powder was added on the basis of the liquid medium.

2. Preparation of the Microbial Agent YF

*B. sonorensis* B-2 and N-16, *B. pumilus* N-17, and *B. paralicheniformis* B-26 preserved at an ultra-low temperature were activated for 24 h, single colonies thereof were inoculated separately to prepare seed fermentation broths. The seed fermentation broth was transferred to a fermentation tank at a ratio of 6% and cultivated at 30° C. and 180 rpm/min under shaking, for 48 h to obtain a fermentation broth. Four bacterial solutions obtained were thoroughly mixed at a ratio of 1:1:1:1, and a resulting mixed bacterial solution was prepared into a powder through peat adsorption.

Example 1

The microbial agent YF (100kg) was composed mainly of the following components: a microbial powder prepared with *B. sonorensis* B-2 and N-16, *B. pumilus* N-17, and *B. paralicheniformis* B-26 as functional bacteria: 54 kg (four strain powders were mixed at a mass ratio of 1:1:1:1), humic acid: 5 kg, calcium sulfate: 400 g (0.4%), zinc sulfate: 200) g (0.2%), ferrous sulfate: 200 g (0.2%), potassium sulfate:

200 g (0.2%), and decomposed sheep dung (as a carrier): 40 kg. The above components were thoroughly mixed to prepare the microbial agent YF, which had a viable count of *Bacillus* reaching greater than 1 billion CFU/g and was preserved at a low temperature.

A content of each component of the microbial agent YF in this example of the present disclosure was shown in Table 3.

TABLE 3

Content of each component in this example

| | Microbial powder (kg) | Humic acid (kg) | Calcium sulfate (g) | Zinc Sulfate (g) | Ferrous sulfate (g) | Potassium sulfate (g) | Carrier (kg) |
|---|---|---|---|---|---|---|---|
| Example 1 | 54 | 5 | 400 | 200 | 200 | 200 | 40 |
| Example 2 | 50 | 5 | 400 | 200 | 200 | 200 | 44 |
| Example 3 | 58 | 5 | 400 | 200 | 200 | 200 | 36 |
| Example 4 | 56 | 3 | 400 | 200 | 200 | 200 | 40 |
| Example 5 | 50 | 8 | 800 | 400 | 400 | 400 | 40 |
| Example 6 | 50 | 7 | 1200 | 600 | 600 | 600 | 40 |
| Example 7 | 57 | 5 | 1200 | 600 | 600 | 600 | 35 |
| Example 8 | 48 | 6 | 400 | 200 | 200 | 200 | 45 |

Test Example 1

The composition formula in the optimal Example 1 was used in all test examples.

1) Determination of the Biological Activity of the Microbial Agent YF (1) Mixing of the Microbial Agent YF with Soil in a Corn Farmland in Saline-Alkali Land Waxy corn (Hannuozao 60) was cultivated in the saline-alkali wasteland in Huangquqiao, Pingluo County, Ningxia Hui Autonomous Region. Before corn cultivation, a powder of the microbial agent YF was evenly sprayed on the surface of soil in the farmland (40 kg/mu), and then the land was tilled with a rotary tiller (at a depth of about 20 cm) to thoroughly mix the microbial agent with the soil. Two treatments were designed: microbial agent YF; and blank control CK: no pesticides and fertilizers were applied. A test plot had an area of 60 m$^2$, and 4 replicate plots were set for each treatment. The following studies were all conducted in this experimental field.

(2) Improvement Effect of the Microbial Agent YF on Soil in the Corn Farmland in Saline-Alkali Land:

After corn was cultivated for 45 d (at a milk stage), soil was collected from the farmland 15 cm from a plant and 0 cm to 20 cm in depth), and collected soil samples were sent to the laboratory in an ice box to test soil pH, organic carbon, organic matter, total nitrogen, total phosphorus, nitrate nitrogen, available phosphorus, available potassium, and other physical and chemical indicators. Results were shown in Tables 4 and 5.

TABLE 4

Improvement effect of the microbial agent YF on soil in the corn farmland in saline-alkali land (1)

| | pH | | Organic carbon (g/kg) | | Organic matter (g/kg) | | Available potassium (mg/kg) | |
|---|---|---|---|---|---|---|---|---|
| Treatment | Average value | Effect (%) | Average value | Effect (%) | Average value | Effect (%) | Average value | Effect (%) |
| YF | 8.00b | 1.23 | 10.06 ± 0.06a | 8.64 | 17.40 ± 0.54a | 5.41 | 359.33 ± 0.06a | 24.51 |
| CK | 8.78a | / | 9.57 ± 0.19b | / | 16.50 ± 0.28a | / | 288.33 ± 0.19b | / |

Notes:
Data in each group is an average of 4 replicates, and lowercases indicate a significant difference (Least significant ranges method, $P < 0.05$)

TABLE 5

Improvement effect of the microbial agent YF on soil in the corn farmland in saline-alkali land (2)

| | Total nitrogen (g/kg) | | Total phosphorus (g/kg) | | Nitrate nitrogen (mg/kg) | | Available phosphorus (mg/kg) | |
|---|---|---|---|---|---|---|---|---|
| Treatment | Average value | Effect (%) | Average value | Effect (%) | Average value | Effect (%) | Average value | Effect (%) |
| YF | 0.73 ± 0.02a | 9.02 | 1.06 ± 0.02a | 0.65 | 4.11 ± 0.28a | 98.98 | 131.83 ± 16.65a | −3.61 |
| CK | 0.67 ± 0.03b | / | 1.05 ± 0.05a | / | 2.16 ± 0.41b | / | 134.73 ± 8.97a | / |

Notes:
Data in each group is an average of 4 replicates, and lowercases indicate a significant difference (Least significant ranges method, $P < 0.05$)

(3) Growth-Promoting Effect of the Microbial Agent YF on Corn in Saline-Alkali Land After the waxy corn variety Hannuozao 60 was cultivated in the saline-alkali land for 14 d according to different treatments, an emergence rate was investigated; and after the corn was cultivated for 30 d, a plant height and a stem thickness (a plant circumference at the first node) were measured. The growth-promoting effect of the microbial agent YF on corn in saline-alkali land was calculated, and results were shown in Table 6.

TABLE 6

Growth-promoting effect of the microbial agent YF on corn in saline-alkali land

| Treatment | Emergence rate (%) | | Plant height (cm) | | Stem thickness (a circumference at the first node, cm) | |
|---|---|---|---|---|---|---|
| | Emergence rate | Promotion rate | Plant height | Promotion rate | Stem thickness | Promotion rate |
| YF | 78.94 ± 4.39 a | 107.75 | 64.27 ± 1.11 a | 46.68 | 9.67 ± 0.24 a | 48.54 |
| CK | 41.67 ± 8.95 b | / | 43.87 ± 0.99 b | / | 6.51 ± 0.31 b | / |

Notes:
Data in each group is an average of 4 replicates, and lowercases indicate a significant difference (Least significant ranges method, $P < 0.05$)

(4) Production-Promoting Effect of the Microbial Agent YF on Corn in Saline-Alkali Land At a corn mature stage (approximately 80 d after cultivation), an ear setting rate and the number of productive ears were investigated, and mature corn ears were collected to determine a corn ear length, a fresh weight, a barren tip length, the number of grains per ear, the number of grains per row, and the ear thickness (a circumference in the middle of an ear). The production-promoting effect of the microbial agent YF on corn in saline-alkali land was evaluated, and results were shown in Tables 7 and 8.

TABLE 7

Production-promoting effect of the microbial agent YF on corn in saline-alkali land (1)

| Treatment | Ear thickness (a circumference in the middle, cm) | | Ear length (cm) | | Ear weight (fresh weight, g) | | Number of grains per ear | |
|---|---|---|---|---|---|---|---|---|
| | Average value | Effect (%) | Average value | Effect (%) | Average value | Effect (%) | Average value | Effect (%) |
| YF | 17.2 ± 0.1a | 5.8 | 22.9 ± 0.2a | 16.7 | 364.3 ± 9.5a | 29.9 | 649.1 ± 6.1a | 9.5 |
| CK | 16.2 ± 0.2b | / | 19.6 ± 0.8b | / | 288.0 ± 30b | / | 592.4 ± 7.2b | / |

Notes:
Data in each group is an average of 4 replicates, and lowercases indicate a significant difference (Least significant ranges method, $P < 0.05$)

TABLE 8

Production-promoting effect of the microbial agent YF on corn in saline-alkali land (2)

| Treatment | Number of productive ears | | Barren tip length (cm) | | Number of rows | | Number of grains per row | |
|---|---|---|---|---|---|---|---|---|
| | Average value | Effect (%) | Average value | Effect (%) | Average value | Effect (%) | Average value | Effect (%) |
| YF | 150 ± 1.3a | 210.0 | 1.9 ± 0.2b | 38.70 | 16.5 ± 0.2a | 1.4 | 39.4 ± 0.7a | 8.2 |
| CK | 51 ± 1.8b | / | 3.1 ± 0.2a | / | 16.3 ± 1.1a | / | 36.4 ± 0.6b | / |

Notes:
Data in each group is an average of 4 replicates, and lowercases indicate a significant difference (Least significant ranges method, $P < 0.05$)

(5) Prevention Effect of the Microbial Agent YF for Corn Stem Rot in Saline-Alkali Land An incidence and disease index of corn stem rot in saline-alkali land were investigated at a milk stage of corn, and the incidence was determined mainly based on the presence of disease spots. Grading standard for corn stem rot (damage degree of an individual plant): grade 1: the whole plant grows normally, the middle and lower leaves undergo wilt/yellow wilt symptoms, and the stem base and ears grow normally; grade 3: all leaves of the whole plant undergo wilt symptoms, the stem base and ears grow normally; grade 5: all leaves of the whole plant undergo typical wilt symptoms, the stem base is discolored and slightly water-logged, and the ears are basically normal; grade 7: plant leaves undergo typical wilt symptoms, the stem base is significantly softened but does not fall down, the ears are drooping, and the grains are not full; and grade 9: the whole plant is dead and falls down, vascular bundles of the stem base rupture, and the grains are shriveled. The prevention and treatment effect of the microbial agent YF for corn stem rot in saline-alkali land was shown in Table 9.

TABLE 9

Prevention and treatment effect of the microbial agent YF for corn stem rot in saline-alkali land

| | Incidence (%) | | Disease index | |
|---|---|---|---|---|
| Treatment | Disease spot rate | Control effect (%) | Disease index | Control effect (%) |
| YF | 13.26 ± 1.65 b | 60.22 | 1.48 ± 0.89 b | 73.33 |
| CK | 33.33 ± 2.91a | / | 5.55 ± 1.56a | / |

Notes:
Data in each group is an average of 4 replicates, and lowercases indicate a significant difference (Least significant ranges method, P < 0.05)

Test Example 2

Figure 6:
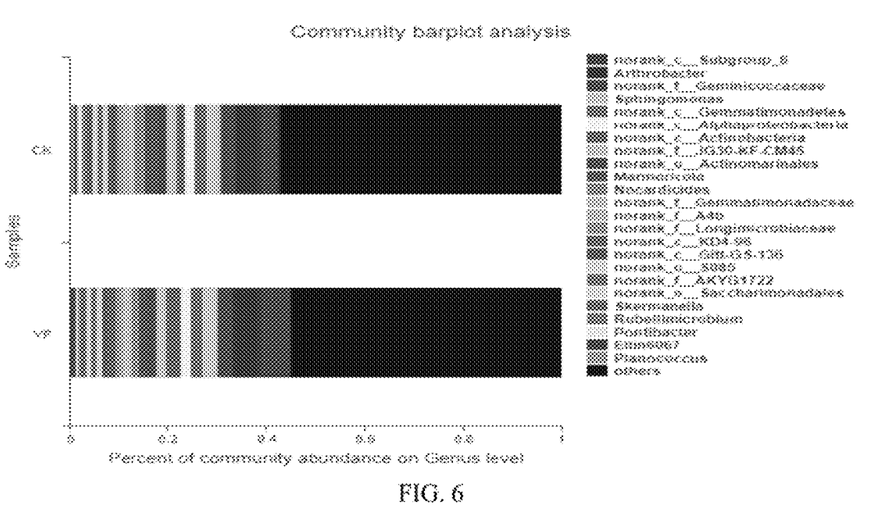
FIG. 6 shows the effect of the microbial agent on a soil bacterial community structure in a corn field.

Microecological Regulation Effect of the Microbial Agent YF on Soil in a Corn Field in Saline-Alkali Land (1) Effect of the Microbial Agent YF on a Soil Microbial Community Structure in the Corn Field in Saline-Alkali Land At a milk stage acorn, soil was collected from the farmland (15 cm from a plant and 0 cm to 20 cm in depth), and collected soil samples were sent to the laboratory in an ice box. The total genomic DNA (gDNA) was extracted from soil samples in each treatment group, and then 1% agarose gel electrophoresis was used to test extracted gDNA. The following bacterial amplification primers were used to conduct PCR amplification for variable regions V3 to V4 of the bacterial 16S rRNA gene: 338F: 5'-barcode-ACTCC-TACGGGAGGCAGCA-3', and 806R: 5'-GGAC-TACHVGGTWTCTAAT-3'. The primers were designed and synthesized by Shanghai Majorbio Bio-Pharm Technology Co., Ltd., where specific primers with barcode were synthesized according to a sequenced region. The formal PCR test adopted a 20 μL reaction system: 10×PCR Buffer: 2 μL, 2.5 mmol/L. dNTPs: 2 μL, 5 μmol/L forward primer: 0.8 μL, 5 μmol/L reverse primer: 0.8 μL, rTaq Polymerase: 0.2 μL, BSA: 0.2 μL, Template DNA: 10 ng, and ddH$_2$O: the balance. PCR amplification conditions: 95° C. for 3 min; cycle number×(95° C. for 30 s, 55° C. for 30 s); and 72° C. for 45 s); 72° C. for 10 min; and 10° C. until the end of the reaction. The second round of PCR amplification products were detected using 2% agarose gel electrophoresis, and then the PCR products were cut and recovered, and eluted with Tris-HCl; and elution products were detected using 2% agarose electrophoresis. The PCR products were quantitatively detected with a QuantiFluor™-ST blue fluorescence quantification system (Promega), and then mixed in a corresponding ratio. A mixed product was sequenced on the Miseq 2×300 platform of Illumina. The effect of the microbial agent YF on a soil bacterial community structure in the corn field in saline-alkali land was shown in FIG. 6.

Figure 7:
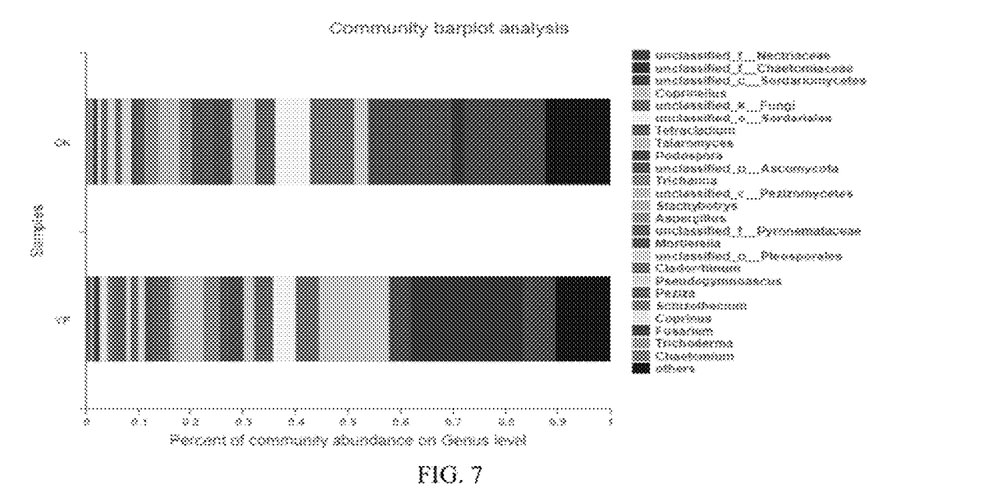
FIG. 7 shows the effect of the microbial agent on a soil fungal community structure in a corn field.

The following fungal amplification primers were used to conduct PCR amplification for regions ITS1 to ITS2: ITS1F: 5'-TCCGTAGGTGAACCTGCGC-3', and ITS2R: 5'-CTCGGACGAGGATCCTCGCC-3'. PCR system for ITS amplification (25 μL): ddH$_2$O: 17.25 μL, Buffer 1: 2.5 μL, dNTPs: 2 μL, primer ITS1F: 1 μL, primer ITS2R: 1 μ, HiFi enzyme: 0.25 μL, and template DNA: 1 μL. PCR reaction conditions: predenaturation at 93° C. for 3 min, denaturation at 93° C. for 45 s, renaturation at 57° C. for 45 s, and extension at 72° C. for 90 s, with 35 cycles. Amplification products were recovered, and sequenced by Shanghai Majorbio Bio-Pharm Technology Co., Ltd. The effect of the microbial agent YF on a soil fungal community structure in the corn field in saline-alkali land was shown in FIG. 7.

Figure 8:
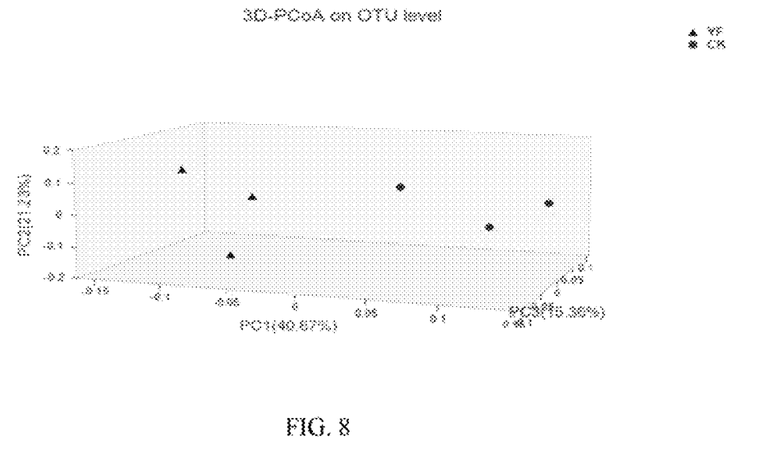
FIG. 8 shows the principal coordinate analysis (PCoA) (OTU level) of a soil bacterial community in a corn field applied with the microbial agent.
Figure 9:
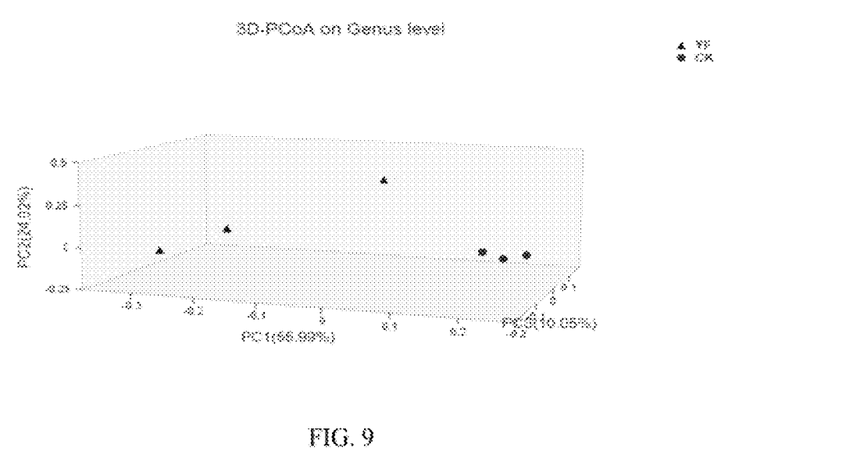
FIG. 9 shows the PCoA (OTU level) of a soil fungal community in a corn field applied with the microbial agent YF.

(2) Effect of the Microbial Agent YF on the Diversity of a Soil Microbial Community in the Corn Field in Saline-Alkali Land Raw data obtained by high-throughput sequencing were subjected to quality control and software splicing to filter out low-quality sequences. Effective sequences with similarity ≥97% were clustered into operational taxonomic units (OTUs). Then single-sample composition analysis was conducted using the QIIME software, and the Coverage, Chao, Shannon, and other indexes were calculated for a sample. The larger the Shannoneven value, the lower the community uniformity. The larger the Shannon value, the higher the community diversity. Coverage refers to a coverage index, which characterizes the detection probability of a microbial sample sequence. The higher the Coverage value, the higher the detection probability of a sequence, which can reflect the true situation of microorganisms in a sample. Sobs refers to an abundance index, and the greater the value, the higher the abundance. The effect of the microbial agent YF on the diversity of a soil bacterial community in the corn field in saline-alkali land was shown in Table 10 and FIG. 8. The effect of the microbial agent YF on the diversity of a soil fungal community in the corn field in saline-alkali land was shown in Table 11 and FIG. 9.

TABLE 10

Effect of the microbial agent YF on the diversity of a soil bacterial community in the corn field in saline-alkali land

| | Species | Diversity index | | Coverage/% | Uniformity | |
|---|---|---|---|---|---|---|
| Treatment | sobs | shannon | Simpson | coverage | shannoneven | simpsoneven |
| CK | 3066 | 6.5158 | 0.0052 | 0.9819 | 0.8116 | 0.0625 |
| YF | 2833 | 6.4524 | 0.0056 | 0.9801 | 0.8119 | 0.0627 |

TABLE 11

Effect of the microbial agent YF on the diversity of a soil fungal community in the corn field in saline-alkali land

| Treatment | Species sobs | Diversity index | | Coverage/% coverage | Uniformity | |
|---|---|---|---|---|---|---|
| | | shannon | Simpson | | shannoneven | simpsoneven |
| CK | 497 | 4.0299 | 0.0445 | 0.9991 | 0.6491 | 0.0469 |
| YF | 433 | 3.4159 | 0.1167 | 0.9985 | 0.5633 | 0.0211 |

It should be noted that terms "including", "comprising", or any other variants thereof are intended to cover non-exclusive inclusion, such that a process, method, article, or device including a series of elements includes not only those elements but also other elements not explicitly listed, or elements inherent to such a process, method, article, or device. Without more restrictions, the elements defined by the sentence "including a . . . " do not exclude the existence of other identical elements in a process, method, article, or device including the elements.

The above examples are only used for describing the technical solutions of the present disclosure, and are not intended to limit the present disclosure. Although the present disclosure is described in detail with reference to the foregoing examples, those of ordinary skill in the art should understand that they can still modify the technical solutions described in the foregoing examples, or make equivalent substitutions on some technical features therein. These modifications or substitutions do not make the essence of the corresponding technical solutions deviate from the spirit and scope of the technical solutions of the examples of the present disclosure.

Industrial Applicability

The microbial agent provided by the present disclosure can significantly promote the growth of corn, significantly increasing a corn emergence rate, a corn plant height, and a corn stem thickness; the microbial agent can also increase an ear thickness, an ear length, an ear weight, the number of grains per ear, the number of productive ears, and the number of grains per row and reduce a barren tip length for waxy corn; the microbial agent YF has a prominent control effect on corn stem rot in saline-alkali land, and can significantly inhibit a variety of soil-borne pathogens; the microbial agent also shows an obvious microecological regulation effect on the soil of corn fields in saline-alkali land, improving the diversity and structure of fungal and bacterial communities in soil and reducing the abundance of pathogens in soil; and the microbial agent can also well improve the soil of corn fields in saline-alkali land, effectively reducing a soil pH and increasing the contents of organic carbon, nitrate nitrogen, total nitrogen, and available potassium. The microbial agent YF of the present disclosure does not include pathogens, heavy metals, and toxic chemical substances, and thus can be used to treat the soil for corn cultivation without causing additional burden on the soil, which is environmentally-friendly. The microbial agent has important scientific significance and application value for the sustainable development of corn industry and the effective utilization of saline-alkali land resources. Therefore, the present disclosure has prominent industrial applicability.

The invention claimed is:

1. A microbial agent YF, comprising four strains:
Bacillus sonorensis B-2, Bacillus paralicheniformis B-26, Bacillus sonorensis N-16, and Bacillus pumilus N-17, wherein the four strains were all deposited in the China General Microbiological Culture Collection Center (CGMCC) on Mar. 5, 2020;
the Bacillus sonorensis B-2 has a deposit accession number of CGMCC NO. 19454, the Bacillus paralicheniformis B-26 has a deposit accession number of CGMCC NO. 19449, the Bacillus sonorensis N-16 has a deposit accession number of CGMCC NO. 19448, and the Bacillus pumilus N-17 has a deposit accession number of CGMCC NO. 19450; and
growth conditions suitable for the four strains comprise temperature: 30° C. to 37° C., pH greater than 8.0, and Horikoshi I, improved LB-I or improved LB-II medium.

2. The microbial agent YF according to claim 1, wherein the Bacillus sonorensis B-2, the Bacillus paralicheniformis B-26, the Bacillus sonorensis N-16, and the Bacillus pumilus N-17 are at a mass ratio of 1:1:1:1; and a viable count of Bacillus in the microbial agent YF is greater than 1 billion CFU/g.

3. A microbial agent YF, wherein the microbial agent YF comprises a bacterial powder prepared from the four strains according to claim 2, and the microbial agent YF further comprises a carrier, humic acid, a conditioning agent, and trace elements; and the content of each component in the microbial agent YF comprises:
48% to 58% of the bacterial powder, 35% to 45% of the carrier, 3% to 8% of the humic acid, 0.4% to 1.2% of the conditioning agent, and 0.6% to 1.8% of the trace elements.

4. The microbial agent YF according to claim 3, wherein the carrier is sheep dung; the conditioning agent is calcium sulfate ($CaSO_4 \cdot 2H_2O$); and the trace elements comprise zinc sulfate ($ZnSO_4$), ferrous sulfate ($FeSO_4 \cdot 7H_2O$), and potassium sulfate ($K_2SO_4$).

5. The microbial agent YF according to claim 4, wherein content of each component in the microbial agent YF comprises:
48% to 58% of the bacterial powder, 35% to 45% of the carrier, 3% to 8% of the humic acid, 0.4% to 1.2% of the calcium sulfate, 0.2% to 0.6% of the zinc sulfate, 0.2% to 0.6% of the ferrous sulfate, and 0.2% to 0.6% of the potassium sulfate.

6. The microbial agent YF according to claim 4, wherein the carrier is decomposed sheep dung.

7. The microbial agent YF according to claim 5, wherein the content of each component in the microbial agent YF comprises:
54% of the bacterial powder, 40% of the carrier, 5% of the humic acid, 0.4% of the calcium sulfate, 0.2% of the zinc sulfate, 0.2% of the ferrous sulfate, and 0.2% of the potassium sulfate.

8. A method of using the microbial agent YF according to claim 1 in a preparation of a drug for preventing and treating stem rot of corn in saline-alkali land.

9. A method of using the microbial agent YF according to claim 2 in a preparation of a drug for preventing and treating stem rot of corn in saline-alkali land.

10. A method of using the microbial agent YF according to claim 3 in a preparation of a drug for preventing and treating stem rot of corn in saline-alkali land.

11. A method of using the microbial agent YF according to claim 4 in a preparation of a drug for preventing and treating stem rot of corn in saline-alkali land.

12. A method of using the microbial agent YF according to claim 5 in a preparation of a drug for preventing and treating stem rot of corn in saline-alkali land.

13. A method of using the microbial agent YF according to claim 6 in a preparation of a drug for preventing and treating stem rot of corn in saline-alkali land.

14. A method of using the microbial agent YF according to claim 7 in a preparation of a drug for preventing and treating stem rot of corn in saline-alkali land.

* * * * *